United States Patent [19]

Taira et al.

[11] Patent Number: 5,436,330
[45] Date of Patent: Jul. 25, 1995

[54] HAMMERHEAD RIBOZYMES WITH ENHANCED STABILITY PROVIDED BY AN ADDITIONAL 3' HAIRPIN SEQUENCE

[75] Inventors: Kazunari Taira; Masanao Oda, both of Tsukuba; Hideaki Shinshi, Tsuchiura; Kensuke Furukawa, Munakata; Hidekatsu Maeda, Nagareyama, all of Japan

[73] Assignees: Agency of Industrial Science & Technology; Ministry of International Trade & Industry, both of Tokyo, Japan

[21] Appl. No.: 111,444

[22] Filed: Aug. 24, 1993

Related U.S. Application Data

[63] Continuation of Ser. No. 499,787, Mar. 27, 1990, abandoned.

[30] Foreign Application Priority Data

Dec. 19, 1989 [JP] Japan ................................ 1-329831

[51] Int. Cl.⁶ .................... C12N 9/22; C12N 15/66
[52] U.S. Cl. ........................... 536/23.2; 536/23.1; 536/24.5; 435/6; 435/91.21; 435/91.31; 435/172.3; 435/320.1
[58] Field of Search .................. 536/23.1, 23.2, 24.5; 435/6, 91.1, 91.21, 91.3, 91.31, 91.4, 172.3, 320.1

[56] References Cited

PUBLICATIONS

Dzianott et al. (1989), Proc. Natl. Acad. Sci., vol. 86, pp. 4823–4827.

*Primary Examiner*—Jacqueline Stone
*Assistant Examiner*—J. LeGuyader
*Attorney, Agent, or Firm*—Oblon, Spivak, McClelland, Maier, & Neustadt

[57] ABSTRACT

A DNA fragment is disclosed which has connected to the downstream side of a first DNA sequence containing a region coding for the first ribozyme RNA a second DNA sequence containing a region coding for second ribozyme RNA capable of cleaving by self-processing the 3'-terminus site of the first ribozyme RNA subjected to transcription. A ribozyme having the 3'-terminus site thereof self-processed is obtained by effecting transcription of a RNA using as a template a recombinant vector obtained by recombination by the use of the DNA fragment.

8 Claims, 6 Drawing Sheets

HAMMERHEAD RIBOZYMES WITH ENHANCED STABILITY PROVIDED BY AN ADDITIONAL 3' HAIRPIN SEQUENCE

This is a continuation of application Ser. No. 07/499,787, filed on Mar. 27, 1990, now abandoned.

BACKGROUND OF THE INVENTION

1. Field of the Invention

This invention relates to a novel ribozyme, a DNA fragment for the production of the ribozyme, a recombinant vector and a method for the production of the ribozyme.

2. Prior Art Statement

It had been long held that all enzymes are composed of proteins. The time-honored concept of enzymes was shattered in 1981 when a ribozyme, a RNA molecule possessing enzymatic activity, was discovered.

This epochal discovery was made by Professor T. Cech et al. of the University of Colorado, U.S.A. They demonstrated that the ribosomal RNA (rRNA) precursor of tetrahymena, a protozoan, expels the intron (IVS) unnecessary for the transfer of gene information by self-splicing without the aid of any protein ["Nature" Vol 308, pp. 820-825 (1984)].

RNA molecules which possess the function of self-splicing and ribozymes which cleave other RNA molecules have since been discovered.

Recently, J. Haseloff and W. L. Gerlach have taken an interest in a nucleotide sequence held in common among ribozymes of several species of plant viruses and have succeeded in constructing an artificial ribozyme which forms a catalytic site with only 24 bases ["Nature", Vol. 334, pp. 585-591 (1988)].

FIG. 1 illustrates the design of this artificial ribozyme. In the diagram, $5'XXX \ldots XXX^3$ represents the nucleotide sequence of a RNA molecule serving as a substrate.

This artificial ribozyme is composed of a binding site ($_{3'}YYY \ldots YYY_{5'}$) forming a nucleotide pair in recognition of the nucleotide sequence of the RNA molecule serving as a substrate and a catalytically active site possessing 24 specific nucleotide sequences. It effects cleavage of the RNA at the position (indicated by an arrow in the diagram) adjoining the (GUC) part of the substrate RNA.

In the aforementioned X . . . X sequence, the nucleotide sequence indicated by GUC may be changed to some other sequence.

Now, the method proposed by Haseloff et al. for the construction of this artificial ribozyme will be described. Specifically, this construction is effected by synthesizing a DNA possessing a complementary nucleotide sequence of said ribozyme RNA and coding for the ribozyme RNA on the basis of the design of ribozyme mentioned above, inserting the resultant synthetic DNA in a plasmid, transforming the resultant recombinant plasmid into a clone, cleaving the cloned DNA with a restriction enzyme Thereby obtaining a DNA fragment coding for the ribozyme RNA, and performing in vitro transcription using the DNA fragment as a template. It has been demonstrated that, in accordance with this method, three ribozymes differing in nucleotide sequence of binding site are synthesized and these three ribozymes cleave the mRNA corresponding to chloramphenicol acetyl transferase at appropriate positions.

The method described above, however, suffers from the following problems.

As described above, this method obtains the artificial ribozyme by transforming the recombinant plasmid, cleaving the resultant clone with a restriction enzyme thereby giving rise to a linearized DNA coding for the ribozyme RNA, and performing transcription using the DNA fragment as a template (run-off transcription; FIG. 2). Thus, this method inevitably entails a treatment with the restriction enzyme. The reason for this treatment of cleavage is that when the ribozyme RNA possesses an extra nucleotide sequence other than a binding site necessary for the recognition of sites of cleavage, there arises the possibility that the extra nucleotide sequence will form a inadvertent base-pairing with a nucleotide sequence other than the cleaving site of the substrate RNA and, as the result, the substrate specificity will be decreased. To prevent this phenomenon, it is necessary to ensure that surplus nucleotide sequences on the 5'-terminus site and the 3'-terminus site are not transcribed when the ribozyme is obtained using the ribozyme-coding plasmid as a template. On the 5'-terminus site, the problem may be solved as by linking the aforementioned DNA to the immediate downstream of any promoters. On the other hand, the control of the 3'-terminus site is more difficult since no universal terminator effective in terminating transcription of an inserted gene such as ribozyme has yet been discovered. The conventional method, therefore, must adopt the so-called run-off method which relies for the treatment of the 3'-terminus site of the DNA template with a restriction enzyme (FIG. 2).

The conventional method necessitates use of a cleaved linear DNA in the transcription entailing the extra work of using the restriction enzyme. While this run-off method allows in vitro synthesis of the ribozyme, it is incapable of effecting in vivo production of the ribozyme while retaining and propagating the recombinant vector including the DNA fragment which codes for the ribozyme RNA. This method experiences difficulty in cleaving and consequently rendering harmless the mRNA originating in a pathogenic virus and, at the same time, allowing the DNA coding for ribozyme to be retained in the vital animal or plant body.

An object of this invention is to provide a novel ribozyme which permits a ribozyme devoid of any surplus nucleotide sequences at its 3'- and 5'-binding sites to be obtained by transcription directly using as a template a circular DNA vector containing the ribozyme gene without necessitating cleavage-with the aforementioned restriction enzyme and also permits in vivo production of the ribozyme while enabling the recombinant vector to be retained and propagated in the vital body. Another object of this invention is to provide a method for the production of the novel ribozyme.

SUMMARY OF THE INVENTION

The present inventors continued a study in search of a ribozyme free from the problem described above. They have consequently found that in the construction of a recombinant vector, the problem mentioned above is solved by coding a second ribozyme DNA sequence to the downstream side of the first DNA sequence including a region coding for the first ribozyme RNA and, at the same time, adding the second transcribed ribozyme sequence capability of cleaving the 3'-terminus site of the transcribed first ribozyme RNA by self-processing. The present invention has been perfected as a result.

To be specific, the present invention is directed to:

1. A DNA fragment having connected to the downstream side of a first DNA sequence containing a region coding for a ribozyme RNA a second DNA sequence containing a region coding for a ribozyme RNA capable of effecting cleavage by self-processing of the 3'-terminus site of the first ribozyme subjected to transcription.

2. A DNA fragment according to Item 1, represented by the following formula:

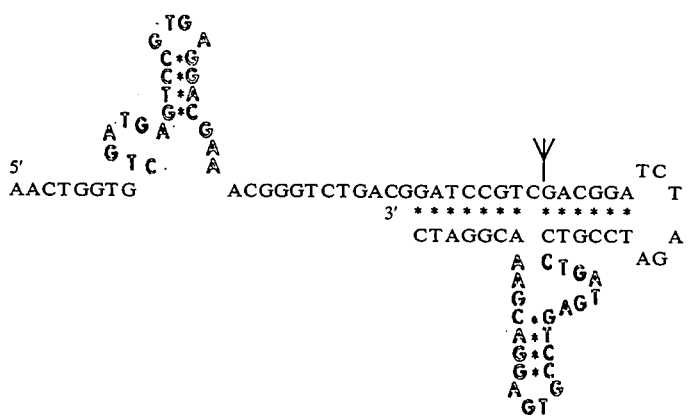

3. A DNA fragment according to Item 1, further having a promoter sequence on the upstream side of the first DNA sequence.

4. A recombinant vector produced by recombination using a DNA fragment set forth in Item 1.

5. A method for the production of a ribozyme having the 3'-terminus site thereof self-processed, which method essentially consists of transcribing a RNA with a recombinant vector according to Item 4 used as a template.

6. A method according to Item 5, wherein the transcription is carried out in vivo.

7. A ribozyme having the 3'-terminus site thereof self-processed, which ribozyme is produced by a method essentially consisting of transcribing a RNA with a recombinant vector of Item 4 as a template.

8. A ribozyme according to Item 7, which ribozyme is represented by the following formula.

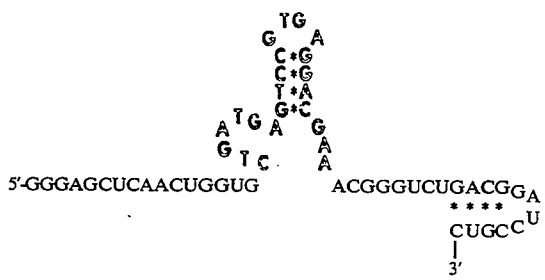

9. A recombinant vector recombined with a DNA fragment of Item 3.

10. A method for the production of a ribozyme having the 3'-terminus site thereof self-processed, which method essentially consists of transcribing a RNA with a recombinant vector of Item 9 as a template.

11. A method according to Item 10, wherein the transcription is carried out in vivo.

12. A ribozyme having the 3'-terminus site thereof self-processed, which ribozyme is produced by a method essentially consists of transcribing a RNA with a recombinant vector of Item 11 as a template.

13. A ribozyme according to Item 12, which ribozyme is represented by the following formula.

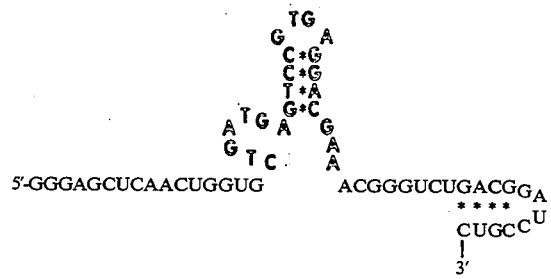

(wherein the asterisk denotes a formed nucleotide pair).

The above and other features and objects of the invention will become apparent with the following detailed description made with reference to the attached drawings.

DETAILED DESCRIPTION OF THE PREFERRED EMBODIMENT

Now, the present invention will be described more specifically below with reference to working examples.

The first DNA sequence which contains a region coding for the aforementioned ribozyme RNA in a DNA fragment inserted in the construction of a recombinant vector according with the present invention comprises a part coding for the catalytically active site of the ribozyme RNA and on its 5'- and 3'-sides parts coding for a binding site capable of recognizing the cleavage position of the substrate RNA.

The second DNA sequence positioned on the downstream side of the first DNA sequence in the DNA fragment serves the purpose of cleaving the 3'-terminus site of the first ribozyme RNA transcribed on the basis of the first DNA sequence and comprises a part coding for the catalytically active site of the ribozyme RNA and parts coding for binding sites capable of recognizing the cleavage position of the 3'-terminus site of the transcribed first ribozyme RNA. The DNA fragment further comprises a DNA sequence coding for the cleaving site where the transcribed RNA is self-processed. This sequence may be a sequence of a region containing a binding site of the 3'-terminus site of the first ribozyme or a region devoid of a binding site as illustrated in FIG. 3.

In the production of a ribozyme by the use of the recombinant vector according with the present invention, the transcription of the ribozyme is carried out with the recombinant vector held in either a test tube or in the vital organism such as yeast mold plant, or animal.

Figure 1:
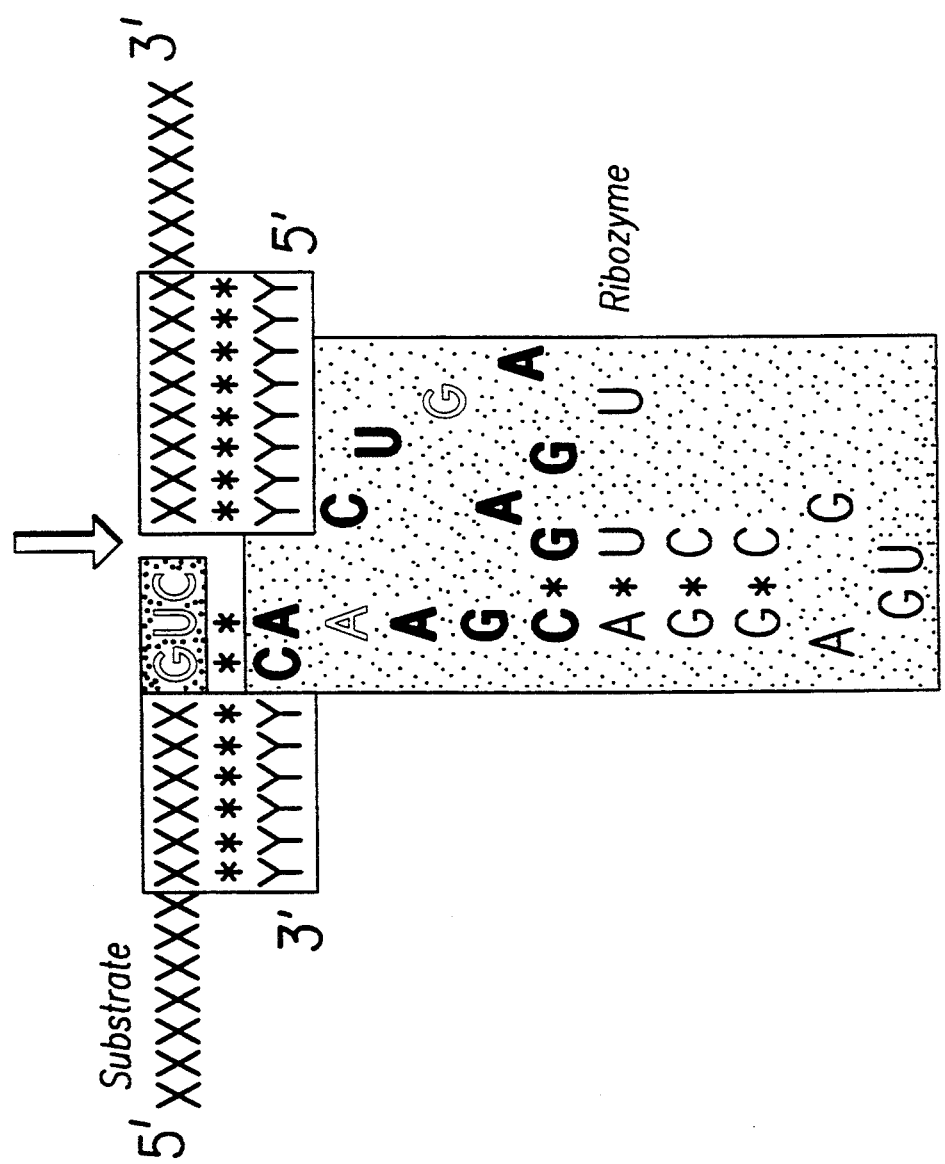
FIG. 1 represents the design of an artificial ribozyme proposed by J. Haseloff et al.
Figure 2:
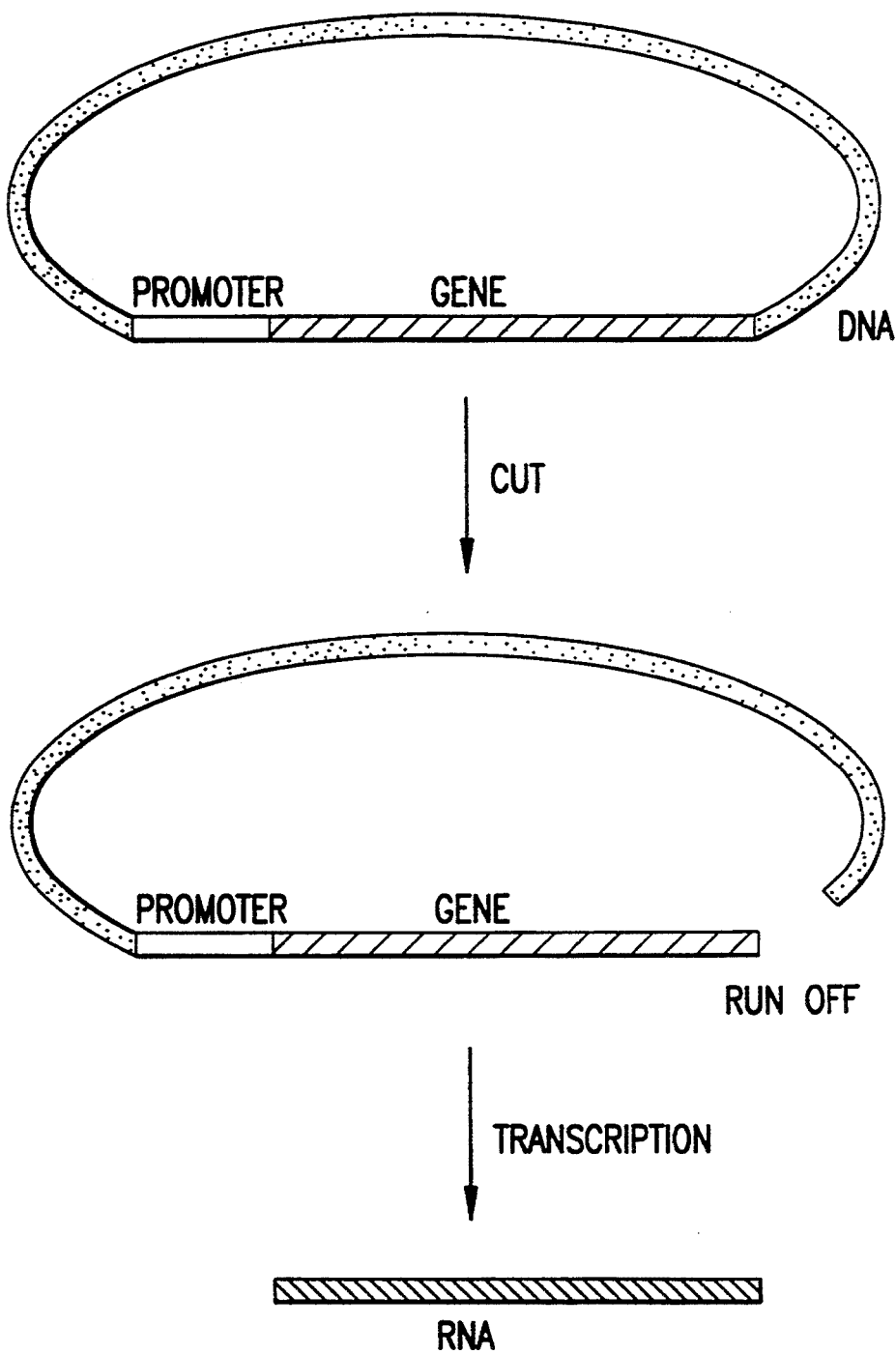
FIG. 2 is a type diagram illustrating a conventional means of ribozyme transcription.
Figure 3:
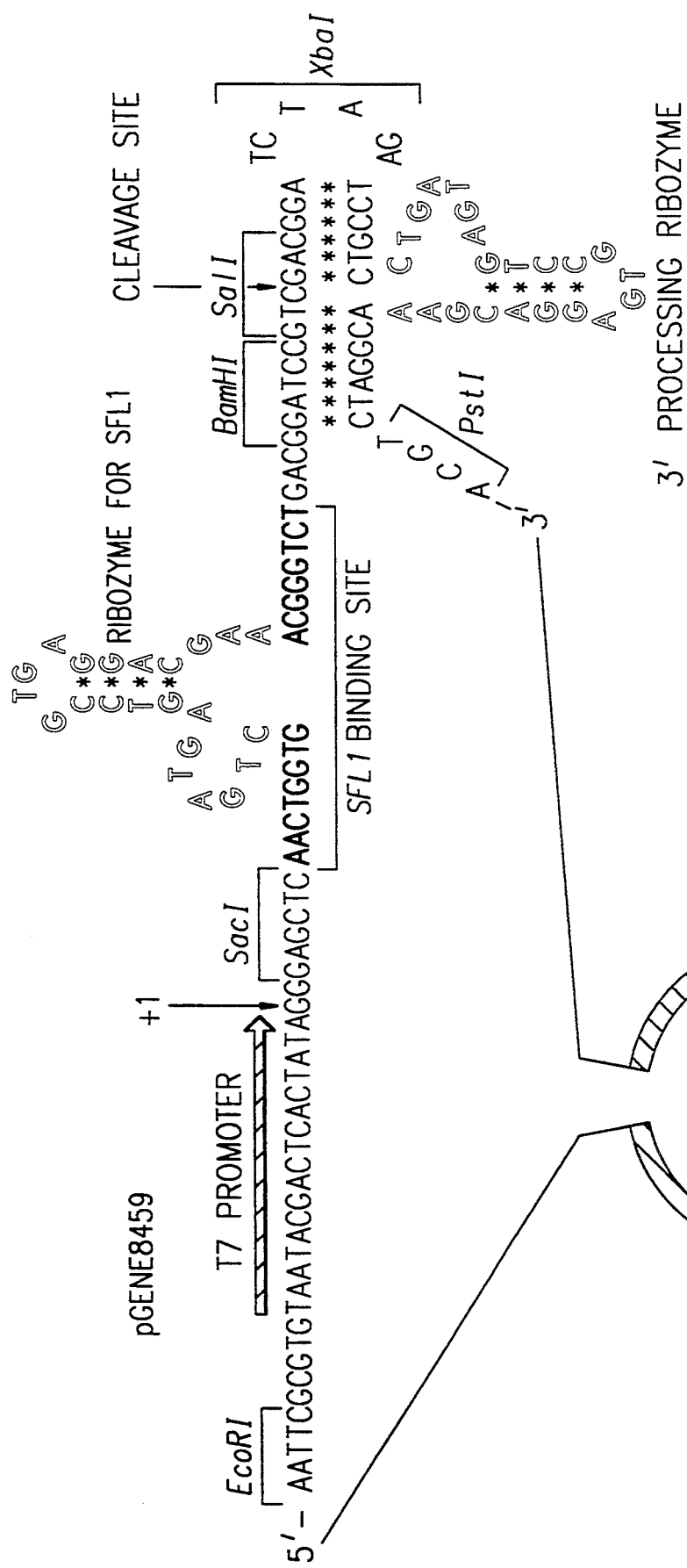
FIG. 3 is a diagram illustrating the configuration of a recombinant plasmid pGENE 8459 according with the present invention.
Figure 6:
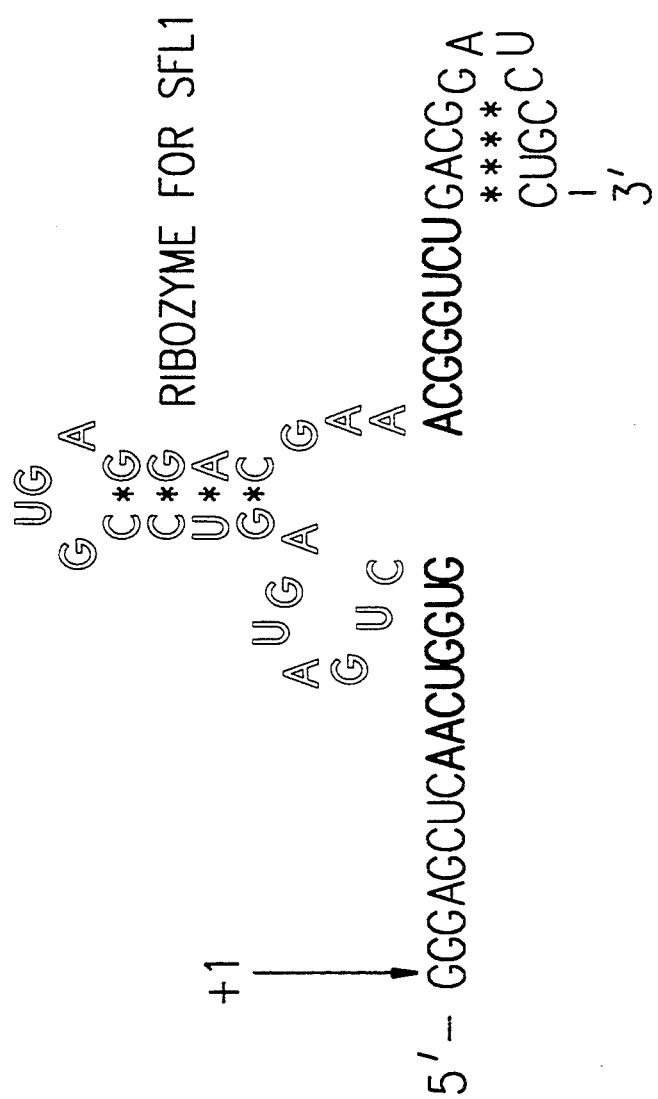
FIG. 6 represents the nucleotide sequence of a ribozyme obtained by the transcription of a recombinant plasmid pGENE 8459 according with the present invention.

The 3'-terminus site of the transcribed ribozyme is cleaved by self-processing and precluded from allowing attachment of any surplus nucleotide sequence thereto or, in the case of the construction of FIG. 3, is enabled to form a nucleotide pair within the surplus nucleotide sequence without affecting the substrate recognition site as shown in FIG. 6.

The points explained above will be described more specifically with reference to FIGS. 3, 4, and 6.

FIG. 3 represents the configuration of a recombinant plasmid, pGENE 8459. This plasmid can cleave an mRNA originating in a yeast suppressor gene for flocculation (hereinafter referred to as "SFL 1"). The recombinant plasmid is prepared by chemically synthesizing six oligonucleotides as illustrated in FIG. 4 by the conventional method, connecting them by phosphorylating the 5'-terminus site thereof, and connecting the connected resultant to a plasmid, pUC119 cleaved with EcoRI and PstI.

The plasmid mentioned above possesses a first DNA part corresponding to a ribozyme RNA comprising a part coding a binding site recognizing the cleaving site of SFL 1 on the downstream side of a promoter for a T7RNA polymerase and a part coding a loop-shaped catalytically active site. It further possesses a second DNA sequence coding for a ribozyme RNA on the downstream side of the first DNA part, comprising a cleavage site for cleaving by self-processing a RNA transcribed, the loop-shaped catalytically active site for the cleavage, and the binding site capable of recognizing the aforementioned cleavage site by self-processing. The DNA sequence which codes for the aforementioned binding site assumes a complementary relation with the cleavage region located downstream of the first ribozyme except for one nucleotide immediately preceding the cleavage site and forms a nucleotide pair.

The plasmid effects sequential transcription of RNA, starting from +1 on the downstream side of the promoter, proceeding through the ribozyme part for SFL 1, and reaching the nucleotide sequence part on the downstream side thereof. Since the transcribed RNA is subjected to self-processing at the aforementioned cleaving site, the subsequent surplus nucleotide sequences are not attached to the produced ribozyme.

The ribozyme RNA which is obtained by effecting transcription using the recombinant plasmid of FIG. 3 used as a template, therefore, possesses a nucleotide sequence of FIG. 6. This ribozyme RNA assumes a hairpin configuration possessing a complementary nucleotide sequence on the 3'-terminus site thereof and forming a nucleotide pair. Owing to this configuration, the ribozyme RNA has stability to resist the action of exonuclease in the vital body.

In the construction of the recombinant plasmid of FIG. 3, a ribozyme for the cleavage of SFL 1 is the ribozyme to be produced, a promoter for the T7RNA polymerase is the promoter, and pUC119 is the vector. This invention is not particularly limited to these substances.

For example, the ribozyme to be produced can be applied to the cleavage of varying RNA's by suitably altering the DNA sequence which codes for the binding site, depending on the nucleotide sequence of the particular RNA subjected to the cleavage. The promoter is not limited to what is mentioned above but may be freely selected from among various promoters including SP6 and GAL 7, for example. Further as regards the recombinant vector since the aforementioned construct is capable of being transcribed into ribozyme RNA's directly from a circular DNA template, the recombinant vector of the present invention may be suitably selected from among vectors and therefore fulfilling their function amply in various vital organisms, depending on the kind of the vital body such as plant or animal.

The recombinant vector containing the DNA fragment possessing the aforementioned first and second DNA sequences according with the present invention is capable of producing directly from a circular DNA template and a ribozyme free from the addition of a surplus nucleotide sequence can be produced without necessitating use of a restriction enzyme. It is, therefore, capable of producing the ribozyme with a simple procedure as compared with the production by the conventional method using a restriction enzyme and, at the same time, allowing the production of the ribozyme while enabling the recombinant vector to be retained and propagated within the vital organism as well. Particularly the ribozyme of the kind of FIG. 6 which is obtained by the present invention acquires a hairpin configuration owing to the formation of a nucleotide pair on the 3'-terminus site thereof and, therefore, enjoys highly satisfactory stability enabling it to withstand the presence of an exonuclease in the vital organism. The present invention contributes immensely to the creation of virus-resistant plants or to the development of novel drugs to combat AIDS viruses, for example.

Now, the present invention will be described more specifically below with reference to a working example.

(1) Construction of recombinant vector

Figure 4:
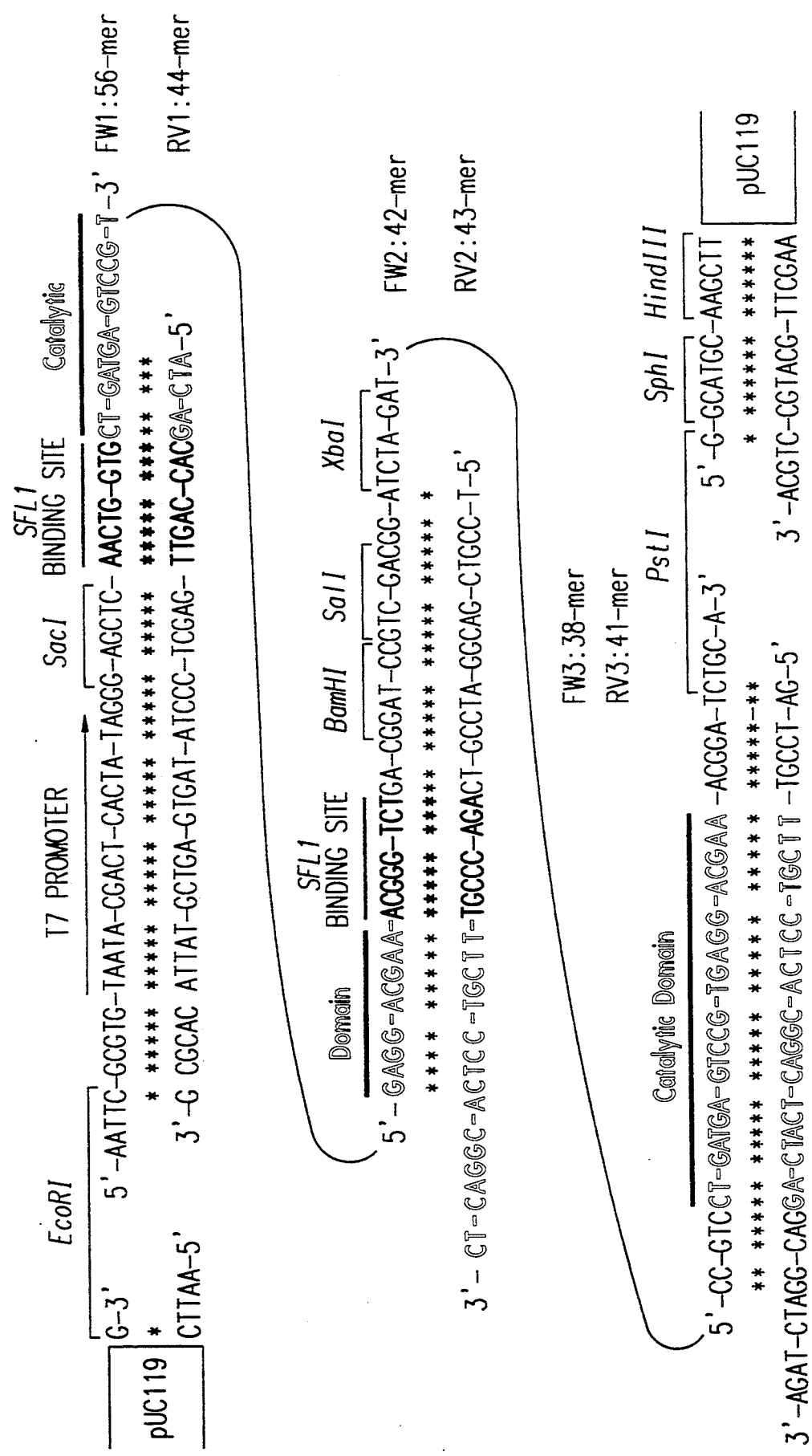
FIG. 4 is a diagram illustrating a method for the construction of a recombinant plasmid pGENE 8459 according with the present invention.

Six oligonucleotides shown in FIG. 4 (FW1, 2, 3, & RV1, 2, 3) were synthesized utilizing a 380B DNA synthesizer (Applied Biosystems) and purified by OPC columns. 5' Phosphorylation was performed on 250 pmol of the OPC purified oliaonucleotides in a total volume of 100 μL solution contianing; 10 μL 10× kinase buffer (250 mM Tris-HCl, pH 7.6, 100 mM DTT, and 100 mM MgCl₂); 25 μL 0.1 mM ATP; and 5 μL T4 polynucleotide kinase (10 units/μL). The phosphorylation reaction was continued at 37° C. for 50 minutes and then the enzyme was inactivated by heating the mixture at 65° C. for 15 minutes. Fifty microliter of the resulting oligonucieotide (2.5 pmol/μL) was mixed with the same volume of its complementary counterpart and kept at 95° C. for two minutes. The mixture was cooled slowly to room temperature. The annealed fragments (ca. 4 pmol each/3.3 μL) were ligated to the EcoRI/PstI double digested pUC119 fragment (<1 pmol) under the described conditions. [1] Hayashi, K., Nakazawa, M., Ishizaki, Y. and Obayashi, A. (1985), "Nucleic Acids Res.," 13, 3261–3271; 2) Hayashi, K., Nakazawa, M., Ishizaki, Y., Hirooka, N., and Obayashi, A. (1985), "Nucleic Acids Res.," 13, 7979–7992].

Competent MV1184 cells were transformed with the ligation mixture and positive clones were selected by digesting with BamHI, whose restriction site had been created inside the ribozyme insert. Single stranded DNAs of the positive clones were prepared and sequencing was performed on a 370A DNA sequencer (Applied Biosystems).

(2) Production of ribozyme

Transcription was carried out in a total volume of 25 μL solution containing; 2 μL 5× transcription buffer (200 mM Tris-HCl, pH 7.5; 30 mM MgCl₂; 10 mM spermidine; 0.05% bovine serum albumin); 1.25 μL 0.2 MDTT; 2.5 μL NTP mix (500 μM each of UTP, ATP, CTP, and GTP); 1.25 μL Human placental ribonuclease inhibitor (20 units/μL); 0.5 μL <α-³²P)CTP (20 μCi/)μL, 800 Ci/mmol); 2.5 μL template DNA solution (pGENE 8459 or pAM19SFL1ΔC; 1 μg/μL); and 0.65 μL T7 RNA polymerase (20 units/μL) (Amersham). The transcription was continued at 37° C. for two hours. The results are shown in the diagram of electrophorsis in FIG. 5.

Figure 5:
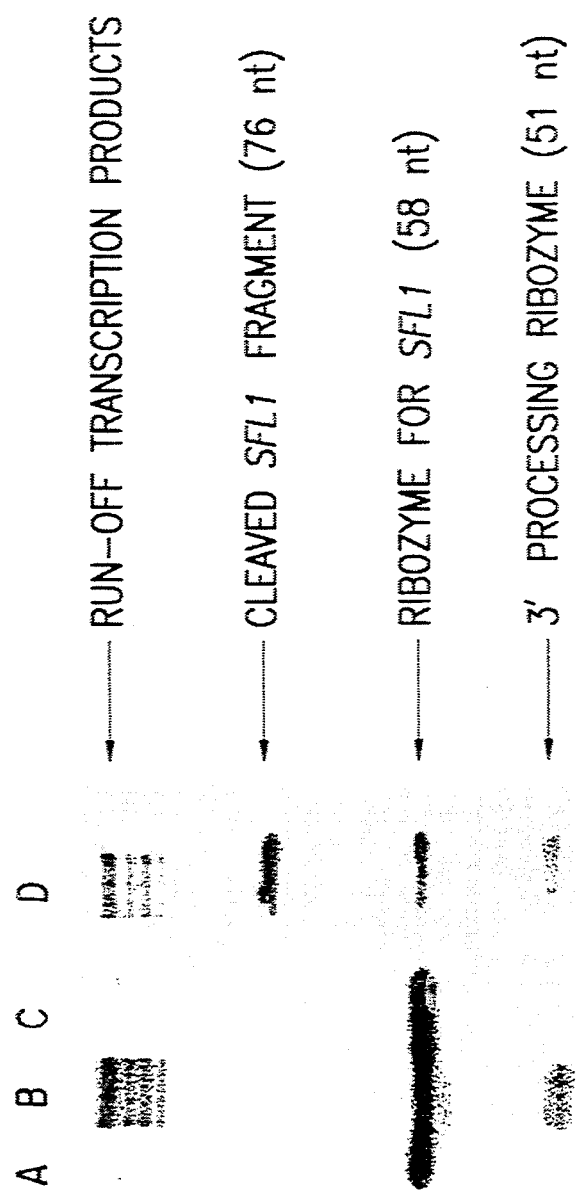
FIG. 5 represents patterns of electrophoresis of various products obtained by the transcription of a recombinant plasmid pGENE 8459 according with the present invention.

In FIG. 5, (A) represents the data obtained by using a circular pGENE 8459 as a template DNA, (B) the data obtained by using a linear pGENE 8459 cleaved with pstI as the template DNA (run-off transcription), (C) the data obtained by using a pGENE 8459 digested with EcoRI as the template DNA, and (D) the data obtained by mixing the equal volume of the run-off transcription products of (B) with a pre-labled SFL1 mRNA which had been produced under the identical conditions described above, in a separate run utilizing T7 promoter/T7 RNA polymerase and the PstI-linearized pAM19SFLΔC and allowing the reaction mixture to stand at 37° C. for 2 hours.

The products of transcription obtained by the procedures A–D mentioned above were labelled with ³²p and analyzed with a 8% polyacrylamide gel containing 25% formamide and 7% urea. The regions ranging approximately from the 50-nucleotide through the 130-nucleotide are shown in FIG. 5.

It can be clearly noted from the results of FIG. 5 that:

A: In the method using a circular pGENE 8459 as a template, a ribozyme for SFL 1 formed with the 58-mer was released because the ribozyme for the treatment of the 3'-terminus site acted efficiently.

B: In the method using as a template a linear pGENE 8459 resulting from the digestion at the PstI site immediately downstream of the 3'-processing ribozyme, the product of a run-off transcription of about 109-nucleotide was formed first and following the action of the 3'-processing ribozyme for SFL 1 resulting two more bands were detected (58-nucleotide and 51-nucleotide).

C: In the method using as a template a linear pGENE 8459 formed by using a EcoRI site located immediately upstream of a T7 promoter, there were obtained entirely the same results as in the method of A.

D: In the method preparing the transcription product of a SFL 1 gene by the use of a T7RNA polymerase and subsequently mixing this product with the run-off transcription products of B, since the SFL1 binding site was designed to base-pair with the SFL1 mRNA of ca. 76 nucleotide region from the transcription initiation site, the appearance of the 76-nucleotide fragment confirms that the released first ribozyme possesses expected substrate specificity and activity against the SFL1 mRNA.

What is claimed is:

1. A ribozyme having the formula:

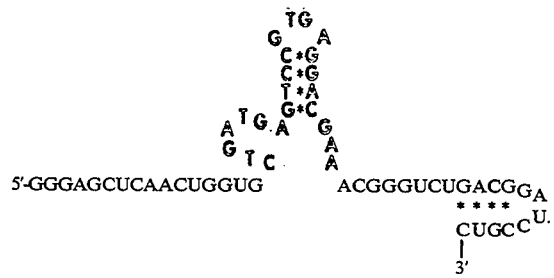

2. A DNA fragment comprising:
(a) a first DNA sequence encoding hammerhead ribozyme RNA, and
(b) a second DNA sequence-covalently linked to the 3'-terminus of said first DNA sequence, said second DNA sequence encoding
(b1) a cleavage site at the 3'-terminus site of RNA transcribed from the said first DNA sequence,
(b2) binding site ribozyme RNA which recognizes and binds to said 3'-terminus site of RNA transcribed from said first DNA sequence, and
(b3) catalytic hammerhead ribozyme RNA capable of cleaving said transcribed RNA at said 3'-terminus site, wherein said first DNA sequence encodes hammerhead ribozyme RNA which acquires a hairpin configuration due to formation of a nucleotide pair on the 3'-terminus end of said hammerhead ribozyme RNA.

3. The DNA fragment of claim 2, comprising the following sequence:

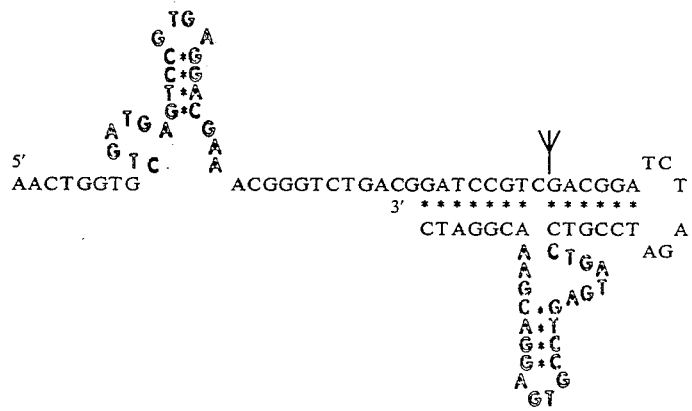

wherein the symbol ↓ identifies said cleavage site.

4. The DNA fragment of claim 2, having an RNA polymerase promoter sequence operably covalently linked to the 5'-terminus thereof.

5. A recombinant vector comprising the DNA fragment of claim 2.

6. A recombinant vector comprising an RNA polymerase promoter operably covalently linked to the DNA fragment of claim 2.

7. The recombinant vector of claim 5, wherein said DNA has the sequence:

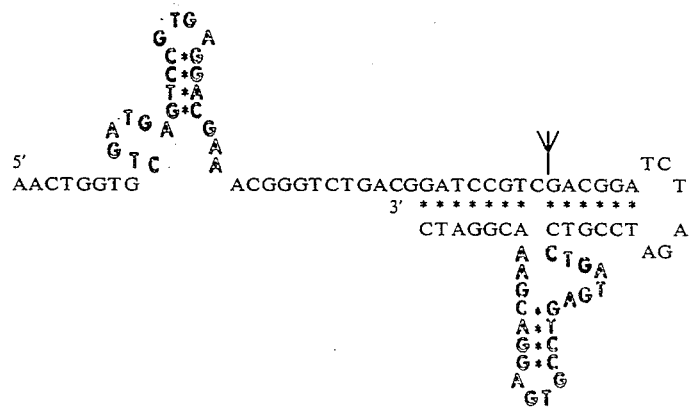

wherein the symbol ↓ identifies said cleavage site.

8. The recombinant vector of claim 7, further comprising an RNA polymerase promoter sequence operably covalently linked to the 5'-terminus of said DNA sequence.

* * * * *